United States Patent [19]

Spies

[11] Plant 4,835

[45] Apr. 6, 1982

[54] LIGHT PINK MINIATURE ROSE

[75] Inventor: Mark C. Spies, Arlington, Va.

[73] Assignee: Nor'East Miniature Roses, Inc., Rowley, Mass.

[21] Appl. No.: 189,796

[22] Filed: Sep. 22, 1980

[51] Int. Cl.[3] ..... A01H 5/00

[52] U.S. Cl. ..... Plt./9

[58] Field of Search ..... Plt./11

*Primary Examiner*—James R. Feyrer

*Attorney, Agent, or Firm*—Vincent G. Gioia

[57] ABSTRACT

A new light pink miniature rose.

1 Drawing Figure

The present invention relates to a new and distinct variety of rose plant of the miniature rose class, which was originated by my crossing as seed parent the rose known as "Gene Boerner" and my unpatented, unreleased seedling of the cross "Gay Princess" × "Yellow Jewel" as pollen parent.

Among the novel characteristics possessed by this new variety which distinguish it from its parents and all other varieties of which I am aware are unusually clean Venetian pink colored flowers of heavy petalage borne primarily singly to a stem in a manner typical of hybrid tea plants but sometimes in clusters of up to 5 blooms. The flowers are especially long lasting on the plant and after cutting. Asexual reproduction by budding of the new variety as performed in Essex County, Mass., shows that the foregoing and other distinguishing characteristics come true to form and are established and transmitted through succeeding propagations.

The new and improved rose variety which I have developed is an unusual combination of light pink color and hybrid tea-like form with good substance and substantially non-fading. The plant is attractive, vigorous and well proportioned.

The accompanying drawing shows typical specimens of the vegetative growth and flowers of the new variety in different stages of development and as depicted in color as nearly true as it is reasonably possible to make the same in color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "49B" is plate 49B of the Royal Horticultural Society Color Chart.

Parentage: Seedling.

*Seed parent.*—"Gene Boerner".

*Pollen parent.*—("Gay Princess" × "Yellow Jewel").

Class: Miniature.

The following observations are made of specimens grown in Essex County, Mass., during the month of July.

FLOWER

Blooming habit: Recurrent, near continuous.

A. Bud:

(1) *Size.*—Medium.

(2) *Form.*—Ovate.

(3) *Color.*—When sepals first divide — 49B to 49C. When petals begin to unfurl — 49D with 50D washing (undersurface of petals first visible as outer petals unfurl).

(4) *Sepals.*—Smooth, short, slight foliation.

(5) *Peduncle.*—Length — about $\frac{3}{4}$ to $1\frac{1}{2}$ inches. Aspect — straight. Strength — erect, strong. Color — 145A.

B. Bloom:

(1) *Size.*—Average size when fully expanded — about $1\frac{1}{2}$ inches.

(2) *Borne.*—Primarily singly, but also clusters of up to five blooms.

(3) *Form.*—High centered, becoming flat upon opening.

(4) *Petalage.*—Number of petals under normal conditions — about 55 to 60.

(5) *Color.*—(during first two days) High centered clean Venetian pink buds unfurl into heavy petaled hybrid tea-like blooms retaining similar color range through opening and aging. Some slight washing of slightly deeper tonality pink coloring may be seen on petal undersurface. Color range tends to be 49B through 49D and overall tonality resembles 50D. Fully open blooms show 49D and 56D coloring upon aging. At point of petal attachment color is very white approaching 155B.

C. Petals:

(1) *Texture.*—Firm.

(2) *Appearance.*—Inside — satiny; outside — satiny.

(3) *Form.*—Rounded, petals relatively wide, in older blooms petals quil and fold under.

(4) *Arrangement.*—Shingle-like.

(5) *Petaloids in center.*—10 to 15.

(6) *Persistence.*—Drop cleanly.

(7) *Fragrance.*—Slight.

(8) *Lasting quality.*—Very long on plant and as cut flower.

REPRODUCTIVE ORGANS

A. Stamens, filaments and anthers:

(1) *Arrangement.*—Stamens regularly arranged around styles.

(2) *Color.*—Orange yellow.

B. Pollen:

*Color.*—Orange yellow.

C. Styles: Uneven, medium length.

D. Stigmas:

*Color.*—Greenish yellow.

E. Hips: None observed.

PLANT

A. Form: Compact, rounded.

B. Growth: Very vigorous, uniform branching.
*Height attained.*—12 to 15 inches.

C. Foliage: Compound 5 to 7 leaflet leaves.
(1) *Size.*—Medium.
(2) *Quantity.*—Abundant.
(3) *Color.*—Upper side — near 131A; under side — near 131A.
(4) *Shape.*—Pointed, oval.
(5) *Texture.*—Upper side — glossy; under side — matte.
(6) *Edge.*—Serrated.
(7) *Serration.*—Large, extend nearly around leaflet.
(8) *Leaf stem.*—Color — near to 152A; under side — near to 144C.
(9) *Stipules.*—Medium length.
(10) *Resistance to disease.*—Blackspot — average. Mildew — average.

D. Wood:
(1) *New wood.*—Color — near 143C. Bark — smooth.
(2) *Old wood.*—Color — near to 144A. Bark — smooth.

E. Thorns:
(1) *Thorns.*—Quantity — almost none. On laterals from stalk — practically none. Form — short, thin, pointed. Color (when young) — 161B. Position — irregular and rare.
(2) *Prickles.*—None.

F. Winter hardiness: Needs normal protection in extreme climate.

I claim:

1. A new and distinct variety of rose plant of the miniature class, substantially as shown and described, characterized particularly by Venetian pink blooms borne on a vigorous, compact, well rounded plant of attractive foliage.

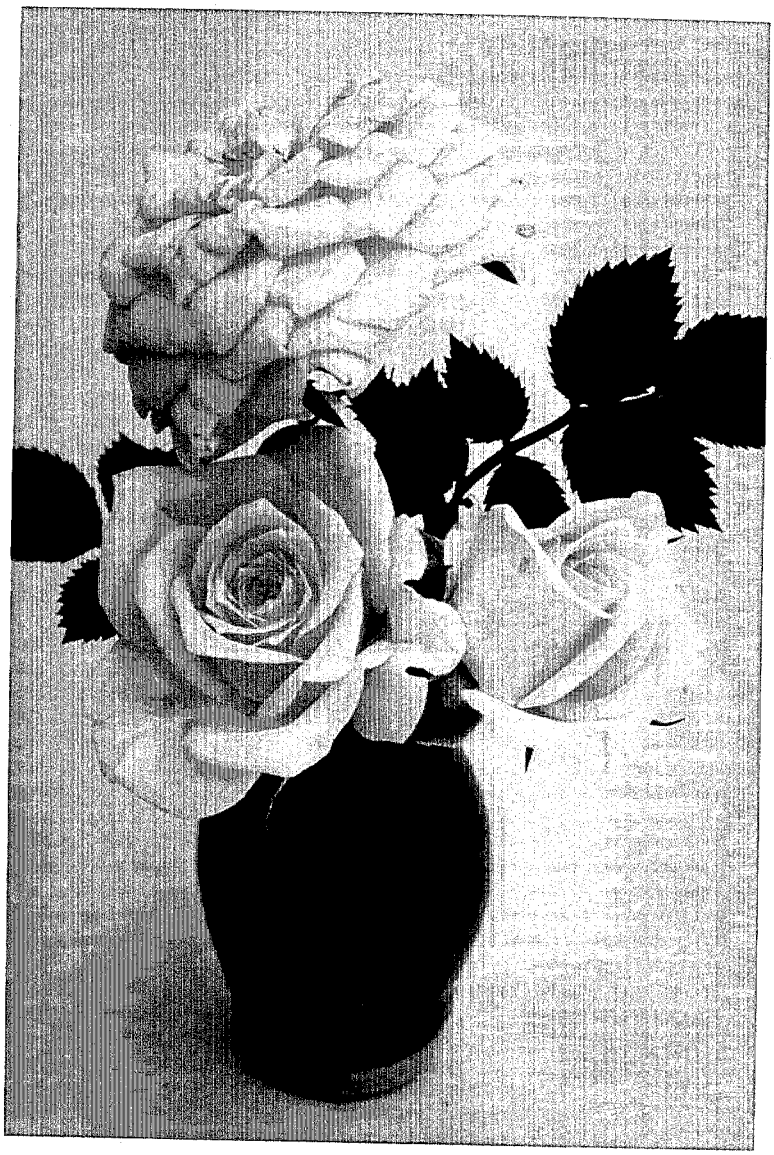

* * * * *